United States Patent
Barr et al.

(10) Patent No.: US 6,376,524 B1
(45) Date of Patent: Apr. 23, 2002

(54) TRIPHENYL COMPOUNDS AS INTERLEUKIN-4 ANTAGONISTS

(75) Inventors: Kenneth J. Barr, San Francisco; Brian C. Cunningham, San Mateo; William Michael Flanagan, Menlo Park; Wanli Lu, Palo Alto; Brian C. Raimundo; Nathan D. Waal, both of San Francisco; Jennifer Wilkinson, Redwood City; Jiang Zhu, San Jose; Wenjin Yang, Foster City, all of CA (US)

(73) Assignee: Sunesis Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/602,546

(22) Filed: Jun. 21, 2000

(51) Int. Cl.$^7$ .................. A61K 31/085; A61K 31/166; A61K 31/41; C07C 39/02; C07C 43/205

(52) U.S. Cl. ............... 514/381; 514/617; 514/646; 514/728; 548/250; 548/252; 564/170; 564/174; 568/636; 568/638; 568/643

(58) Field of Search ............... 548/250, 252; 564/170, 174; 568/636, 638, 643; 514/381, 646, 617, 728

(56) References Cited

U.S. PATENT DOCUMENTS

| | | | | |
|---|---|---|---|---|
| 3,987,102 A | * | 10/1976 | Karrer et al. | 260/590 D |
| 3,991,049 A | | 11/1976 | Siegrist et al. | 260/240 |
| 5,756,545 A | | 5/1998 | O'Brien et al. | 514/562 |
| 5,874,473 A | | 2/1999 | Kluender et al. | 514/570 |

FOREIGN PATENT DOCUMENTS

| | | | |
|---|---|---|---|
| BE | 837.403 | | 7/1976 |
| JP | 04-122680 | * | 4/1992 |
| WO | WO 96/15096 | | 5/1996 |
| WO | WO 97/20815 | | 6/1997 |
| WO | WO 97/40017 | | 10/1997 |
| WO | WO 98/26773 | | 6/1998 |
| WO | WO 98/42670 | | 10/1998 |
| WO | WO 98/43971 | | 10/1998 |
| WO | WO 99/01127 | | 1/1999 |
| WO | WO 99/32150 | | 7/1999 |
| WO | WO 00/15614 | | 3/2000 |
| WO | WO-00/21368 | * | 4/2000 |

OTHER PUBLICATIONS

Perrier et al., Chemical Abstracts, 130:296195, 1999.*
Varoli et al., Chemical Abstracts, 110:261, 1989.*

* cited by examiner

Primary Examiner—Fiona T. Powers
(74) Attorney, Agent, or Firm—Heller Ehrman White & McAuliffe LLP

(57) ABSTRACT

Triphenyl compounds of the formulae I, II, and VI:

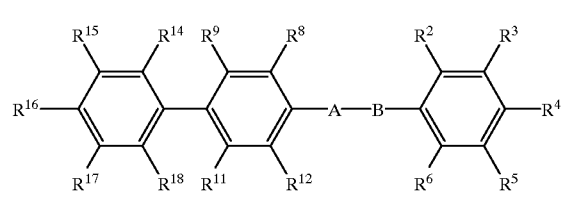

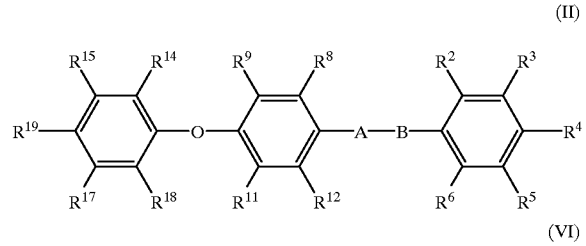

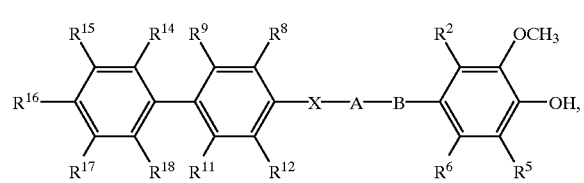

methods of making them, pharmaceutical compositions containing them, and methods for their use. The compounds are compounds are interleukin-4 antagonists; and are useful for the treatment of asthma and allergies.

15 Claims, No Drawings

TRIPHENYL COMPOUNDS AS INTERLEUKIN-4 ANTAGONISTS

BACKGROUND OF THE INVENTION

1. Field of the Invention

This invention relates to antagonists of interleukin-4 signaling. In particular, this invention relates to certain triphenyl compounds that antagonize interleukin-4 signaling, to methods of making them, to pharmaceutical compositions containing them, and to their uses.

2. Description of the Related Art

Interleukin-4 (IL-4) is a pleiotropic cytokine that is produced primarily by T helper type 2 lymphocytes (TH2 cells). The most clinically significant activity of this cytokine is the stimulation of immunoglobin class switching of the immune system's B-cells to IgE production. See P. Chomarat et al., "An update on interleukin-4 and its receptor", *Eur. Cytokine Netw.*, 8(4), 333–344 (1997); R. A. Pauwels et al., "Cytokines and their receptors as therapeutic targets in asthma", *Clin. Exp. Allergy*, 28(Suppl. 3), 1–5 (1998), and references discussed therein.

Ample evidence exists that antagonism of IL-4 can alleviate allergic responses. These include the correlation of allergy and asthma symptoms with IL-4 levels in both allergen immunotherapy and asthma patients, the reduction of spontaneous IgE production in lymphocytes following treatment with IL-4 antibodies, and the inability to induce asthma-associated eosinophilia in IL-4 gene knockout mice. Additional evidence exists correlating elevated levels of IL4 with osteoporosis, osteoarthritis, rheumatoid arthritis, and autoimmune and other inflammation related disorders. Antagonism of IL-4 might further prove useful for therapeutically desirable immunosuppression.

The attractiveness of developing a drug that antagonizes IL4 activity has not escaped the pharmaceutical industry. Immunex and Wyeth-Ayerst are developing a nebulized form of a soluble IL4 receptor for the treatment of moderate asthma. The drug, Nuvance, is now in Phase II clinical trials. Glaxo SmithKline is developing an IL-4 antibody that is currently in clinical trials for the treatment of asthma.

Small molecule IL-1 antagonists have been sought. See R. Sarabu, "Design and synthesis of small molecule interleukin-1 receptor antagonists based on a benzene template, *Drug Design Discovery*, 15, 191–198 (1998).

It would be desirable to develop a small-molecule IL-4 antagonist.

SUMMARY OF THE INVENTION

In a first aspect, this invention provides compounds of formula I and formula II:

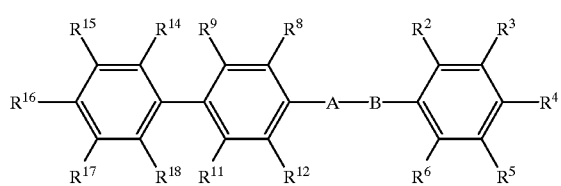

(I)

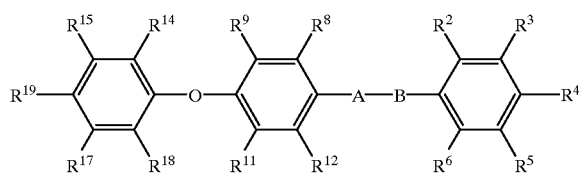

(II)

where:

A—B is selected from the group consisting of —CHR$^X$—CHR$^X$—, —CR$^Y$=CR$^Y$—, —CHR$^Y$—O—, —O—CHR$^Y$—, NR$^1$—C(=O)—, —C(=O)—NR$^1$, —S(O)$_{0\text{-}2}$—CHR$^X$—, —CHR$^X$—S(O)$_{0\text{-}2}$—, —SO$_2$—NR$^1$—, —NR$^1$—SO$_2$—,—C(=O)—CHR$^X$—, —CHR$^X$—C(=O)—, and cycloalkylene;

each R$^X$ is independently selected from the group consisting of hydrogen, hydroxy, alkyl, haloalkyl, aminoalkyl, guanidinoalkyl, alkoxy, amino, alkylamino, dialkylamino, cycloamino, alkylcarbonylamino, guanidino, carboxy, alkoxycarbonyl, and tetrazole;

each R$^Y$ is independently selected from the group consisting of hydrogen, alkyl, haloalkyl, carboxy, and alkoxycarbonyl;

each R$^1$ is independently selected from the group consisting of hydrogen and lower alkyl;

R$^2$ is selected from the group consisting of hydrogen, halo, and hydroxy;

R$^3$ is selected from the group consisting of optionally fluorinated methoxy and optionally fluorinated ethoxy;

R$^4$ is selected from the group consisting of hydrogen, hydroxy, amino, alkylamino, dialkylamino, and cycloamino;

R$^5$ is selected from the group consisting of hydrogen, halo, alkyl, haloalkyl, alkoxy, amino, alkylcarbonylamino, alkylsulfonylamino, benzenesulfonylamino, toluenesulfonylamino, carboxy, aminocarbonyl, alkylaminocarbonyl, dialkylaminocarbonyl, cycloaminocarbonyl, and alkoxycarbonyl;

R$^6$ is selected from the group consisting of hydrogen, halo, and hydroxy;

R$^8$, R$^9$, R$^{11}$, R$^{12}$, R$^{14}$, R$^{15}$, R$^{17}$ and R$^{18}$ are independently selected from the group consisting of hydrogen, halo, alkyl, haloalkyl, methoxy, and ethoxy;

R$^{16}$ is selected from the group consisting of hydrogen, hydroxy, halo, haloalkyl, alkoxy, aminocarbonyl, alkylaminocarbonyl, carboxy, alkoxycarbonyl, —SO$_2$NR$^1{}_2$, and —NR$^1$SO$_2$R$^1$;

R$^{19}$ is selected from the group consisting of hydrogen, hydroxy, halo, haloalkyl, alkoxy, aminocarbonyl, alkylaminocarbonyl, carboxy, alkoxycarbonyl, —SO$_2$NR$^1{}_2$, and —NR$^1$SO$_2$R$^1$;

and compounds of formula VI (VI)

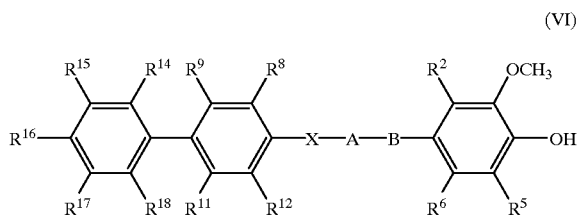

where
X is selected from —CHR$^X$— and —CH$_2$—CHR$^X$—;
A—B is selected from the group consisting of —CHR$^X$—CHR$^X$—, —CR$^Y$═CR$^Y$—, —CHR$^Y$—O—, —O—CHR$^Y$—, —NR$^1$—C(═O)—, —C(═O)—NR$^1$, —S(O)$_{0-2}$—CHR$^X$—, —CHR$^X$—S(O)$_{0-2}$—, —SO$_2$—NR$^1$—, —NR$^1$—SO$_2$—, —C(═O)—CHR$^X$—, —CHR$^X$—C(═O), and cycloalkylene;
each R$^X$ is independently selected from the group consisting of hydrogen, hydroxy, alkyl, haloalkyl, aminoalkyl, guanidinoalkyl, alkoxy, amino, alkylamino, dialkylamino, cycloamino, alkylcarbonylamino, guanidino, carboxy, alkoxycarbonyl, and tetrazole;
each R$^Y$ is independently selected from the group consisting of hydrogen, alkyl, haloalkyl, carboxy, and alkoxycarbonyl;
each R$^1$ is independently selected from the group consisting of hydrogen and lower alkyl;
R$^2$ is selected from the group consisting of hydrogen, halo and hydroxy;
R$^5$ is selected from the group consisting of hydrogen, halo, alkyl, haloalkyl, alkoxy, amino, alkylcarbonylamino, alkylsulfonylamino, benzenesulfonylamino, toluenesulfonylamino, carboxy, aminocarbonyl, alkylaminocarbonyl, dialkylaminocarbonyl, cycloaminocarbonyl, and alkoxycarbonyl;
R$^6$ is selected from the group consisting of hydrogen, halo, and hydroxy;
R$^8$, R$^9$, R$^{11}$, R$^{12}$, R$^{14}$, R$^{15}$, R$^{17}$, and R$^{18}$ are independently selected from the group consisting of hydrogen, halo, alkyl, haloalkyl, methoxy, and ethoxy;
R$^{16}$ is selected from the group consisting of hydrogen, hydroxy, halo, haloalkyl, alkoxy, aminocarbonyl, alkylaminocarbonyl, carboxy, alkoxycarbonyl, —SO$_2$NR$^1_2$, and —NR$^1$SO$_2$R$^1$;
and the pharmaceutically acceptable salts of all these compounds.

In a third aspect, this invention provides pharmaceutical compositions comprising a pharmaceutically acceptable excipient and a therapeutically effective amount of at least one compound of this invention. These compositions find particular use as anti-asthmatic and anti-allergenic agents; and in the treatment of osteoporosis, osteoarthritis, rheumatoid arthritis, and autoimmune and other inflammation related disorders, and for therapeutically desirable immunosuppression.

In a fourth aspect, this invention provides a method of treating an animal having a disease capable of treatment by administration of an IL-4 antagonist, comprising administration to that animal of a therapeutically effective amount of at least one compound of this invention, optionally in conjunction with at least one other conventional therapeutic agent for the disease being treated.

In a fifth aspect, this invention provides methods of preparing the compounds of this invention.

DETAILED DESCRIPTION OF THE PREFERRED EMBODIMENTS

Definitions

"Alkyl" means a linear monovalent hydrocarbyl group having 1 to 5 carbon atoms, or a branched or cyclic hydrocarbyl group having 3 to 5 carbon atoms. Exemplary alkyl groups include methyl, ethyl, isopropyl, cyclopropyl, tert-butyl, cyclopropylmethyl, and pentyl. "Alkoxy" means the group —O-alkyl, where "alkyl" is as defined immediately before.

"Cycloalkylene" means a cyclic hydrocarbyl group having 5 to 7 ring carbon atoms, bonded to an aryl group or other linker atom at both of two adjacent ring carbon atoms; such as 1,2-cyclohexylene. "Cycloalkylene also includes those compounds where the bond between the ring carbon atoms that are bonded to the aryl groups or other linker atoms is a double bond. "Cycloalkylene" specifically includes cyclic compounds as defined immediately before where 1 or 2 of the ring carbon atoms are replaced by O, S, NH, or N-alkyl; such as 2,3-piperidinylene and 3,4-tetrahydropyranylene.

"Cycloamino" means a cyclic amino group having 5 to 7 ring atoms of which at least one is nitrogen and the remainder may all be carbon (e.g. pyrrolidino, piperidino) or one carbon may be replaced by O, S, NH, or N-alkyl (e.g. morpholino, piperazino, and the like).

"Animal" includes humans and non-human mammals, such as companion animals (cats, dogs, and the like) and farm animals (cattle, horses, sheep, goats, swine, and the like).

"Disease" includes any unhealthy condition of an animal, including particularly asthma, allergies, osteoporosis, osteoarthritis, rheumatoid arthritis, and autoimmune and other inflammation related disorders.

"Guanidino" means the group —NH—C(═NH)NH$_2$.

"Halogen" means fluorine, chlorine, or bromine; and "halo" likewise means fluoro, chloro, or bromo. "Haloalkyl" means alkyl (as that term is defined above) substituted with 1 to 5 halogen atoms, especially fluorine or chlorine atoms.

"Optionally fluorinated methoxy" and "optionally fluorinated ethoxy" mean a methoxy group substituted with 0–3 fluorine atoms and an ethoxy group substituted with 0–5 fluorine atoms respectively.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

"Pharmaceutically acceptable salts" means salts that are pharmaceutically acceptable and have the desired pharmacological properties. Such salts include salts that may be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N-methylglucamine, and the like. Such salts also include acid addition salts formed with inorganic acids (e.g. hydrochloric and hydrobromic acids) and organic acids (e.g. acetic acid, citric acid, maleic acid, and the alkane- and arenesulfonic acids such as methanesulfonic acid and benzenesulfonic acid). When there are two acidic groups present, a pharmaceutically acceptable salt may be a mono-acid-mono-salt or a di-salt; and similarly where there are more than two acidic groups present, some or all of such groups can be salified.

A "protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete.

A "therapeutically effective amount" means the amount that, when administered to an animal for treating a disease, is sufficient to effect treatment for that disease.

"Treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The compounds of this invention may possess one or more chiral centers or olefinic bonds, and, if they do, can therefore be produced as individual stereoisomers or as mixtures of stereoisomers, depending on whether individual stereoisomers or mixtures of stereoisomers of the starting materials are used. Unless indicated otherwise, the description or naming of a compound or group of compounds is intended to include both the individual stereoisomers or mixtures (racemic or otherwise) of stereoisomers. Methods for the determination of stereochemistry and the separation of stereoisomers are well known to a person of ordinary skill in the art [see the discussion in Chapter 4 of J. March, "Advanced Organic Chemistry", 4th ed., John Wiley and Sons, New York, N.Y., 1992].

Implicit hydrogen atoms are omitted from the formulae for clarity, but should be understood to be present.

Presently Preferred Compounds

While the broadest definition of the invention is set out in the Summary of the Invention, certain compounds of this invention are presently preferred.

Presently preferred compounds of this invention are compounds of formula III

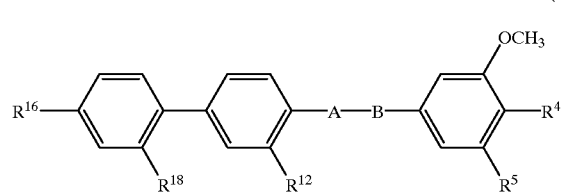

(III)

where:

A—B is —CHR$^X$—CHR$^X$—, —CHR$^Y$—O—, —O—CHR$^Y$—, NR$^1$—C(=O)—, C(=O)—NR$^1$, —SO$_2$—NR$^1$—, —NR$^1$—SO$_2$—;

and R$^X$, R$^Y$, R$^4$, R$^5$, R$^{12}$, R$^{16}$, and R$^{18}$ are as in the Summary of the Invention;

and their pharmaceutically acceptable salts.

More preferred compounds of this invention are compounds of formula IV

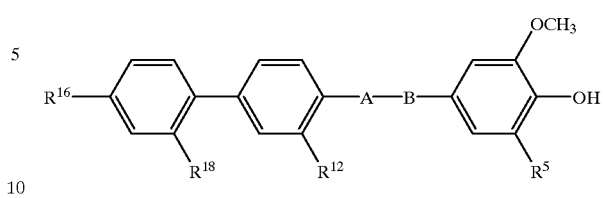

(IV)

where:

A—B is —CHR$^X$—CHR$^X$—, —CHR$^Y$—O—, —O—CHR$^Y$—;

and R$^X$, R$^Y$, R$^5$, R$^{12}$, R$^{16}$, and R$^{18}$ are as in the Summary of the Invention;

and their pharmaceutically acceptable salts.

More preferred compounds of this invention are compounds of formula V

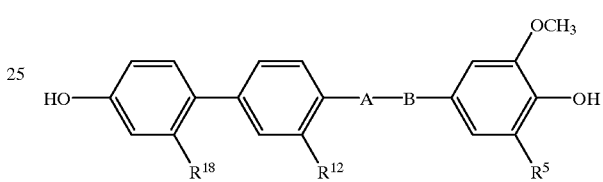

(V)

where:

A—B is —CHR$^X$—CHR$^X$—;

and R$^X$, R$^5$, R$^{12}$, and R$^{18}$ are as in the Summary of the Invention;

and their pharmaceutically acceptable salts.

Preferred compounds of this invention also include those compounds, or groups of compounds discussed above, in which:

(1) at least one of R$^2$, R$^4$, and R$^6$ is not hydrogen;

(2) at least one of R$^{14}$, R$^{15}$, R$^{16}$, R$^{17}$, and R$^{18}$ in formulae I, III, IV, and VI, or at least one of R$^{14}$, R$^{15}$, R$^{17}$, R$^{18}$, and R$^{19}$ in formula II, is not hydrogen;

or both of these preferences are met.

Pharmacology and Utility

The compounds of this invention are antagonists of IL-4 signaling. Their activity as IL-4 signaling antagonists in vitro can be measured by methods such as the STAT6 phosphorylation assay discussed in J. Hon et al., *Science*, 265, 1701–1706 (1994), F. W. Quelle et al., *Mol. Cell Biol.*, 15, 3336–3343 (1995), and K. Takeda et al., *Nature*, 380, 627–630 (1996); and as discussed in Example 3. Their activity can be measured in vivo by activity in the cynomolgus monkey primate model described in C. D. Wegner et al., "Models of Pulmonary Disease: Acute and Chronic Allergic Asthma in the Monkey and Acute and Chronic Viral Pulmonitis in the Mouse" in "Current Protocols in Pharmacology", John Wiley & Sons, 1998, 5.2.1–5.2.19.

The therapeutic ratio of a compound can be determined, for example, by comparing the dose that gives effective anti-asthmatic or anti-allergic activity in a suitable in vivo model such as the cynomolgus model described in Wegner et al., with the dose that gives significant weight loss (or other observable side-effects) in the test animal species.

Pharmaceutical compositions and administration

In general, compounds of this invention will be administered in therapeutically effective amounts by any of the usual modes known in the art, either singly or in combination with at least one other compound of this invention and/or at least one other conventional therapeutic agent for the disease being treated. A therapeutically effective amount may vary widely depending on the disease, its severity, the age and relative health of the animal being treated, the potency of the compound(s), and other factors. Therapeutically effective amounts of compounds of this invention may range from approximately 0.01–100 mg/Kg body weight. A person of ordinary skill in the art will be able without undue experimentation, having regard to that skill and this disclosure, to determine a therapeutically effective amount of a compound of this invention for a given disease.

In general, compounds of this invention will be administered as pharmaceutical compositions by one of the following routes: oral, topical, systemic (e.g. transdermal, intranasal, by inhalation, or by suppository), or parenteral (e.g. intramuscular, subcutaneous, or intravenous injection). Compositions may take the form of tablets, pills, capsules, semisolids, powders, sustained release formulations, solutions, suspensions, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, may be found in such standard references as A. R. Alfonso, "Remington's Pharmaceutical Sciences", 17th ed., Mack Publishing Company, Easton Pa., 1985. Suitable liquid carriers, especially for injectable solutions, include water, aqueous saline solution, aqueous dextrose solution, and glycols.

Typically, compounds of this invention will be administered orally, by inhalation (especially for asthma and in pulmonary inflammatory conditions), or topically (especially for psoriasis). The amount of a compound of this invention in the composition may vary widely depending on the type of composition, size of a unit dosage, kind of excipients, and other factors well known to those of ordinary skill in the art. In general, the final composition may comprise from 0.0001 percent by weight (%w) to 10%w of the compound of this invention, preferably 0.001%w to 1%w, with the remainder being the excipient or excipients.

An composition may optionally contain, in addition to a compound of this invention, at least one other compound of this invention, and/or at least one other agent for the disease state being treated.

Preparation of the Compounds of this Invention

The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser's "Reagents for Organic Synthesis", vols. 1–17, John Wiley and Sons, New York, N.Y., 1991; Rodd's "Chemistry of Carbon Compounds", vols. 1–5 and supplements, Elsevier Science Publishers, 1989; "Organic Reactions", vols. 1–40, John Wiley and Sons, New York, N.Y., 1991; March's "Advanced Organic Chemistry", 4th ed., John Wiley and Sons, New York, N.Y., 1992; and Larock's "Comprehensive Organic Transformations", VCH Publishers, 1989. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

Unless specified to the contrary, the reactions described herein take place at atmospheric pressure over a temperature range between about 0° C. and 125° C.

General synthetic methods are discussed below.

Typically, an appropriately substituted biphenyl or biphenyl ether is reacted with an appropriately substituted benzene to form the linker —A—B— between the biphenyl/biphenyl ether and the benzene.

Where —A—B— is —$CR^Y$=$CR^Y$—, the alkene linker is readily prepared by the either of two methods. In the first method, a suitably substituted aryl aldehyde or ketone is reacted with the sodium salt of a suitably substituted triphenylphosphonium halide (Wittig reaction), prepared from the corresponding halomethyl compound. Thus, for example, a suitably substituted benzyltriphosphonium halide (prepared from the corresponding benzyl bromide) dissolved in a solvent such as tetrahydrofuran is treated with a solution of n-butyllithium at 0° C., stirred at room temperature, then the suitably substituted biphenylaldehyde is added. The reaction is quenched with methanol, extracted, dried, and the extracts concentrated to yield the olefin-linked compound. In the second method, a suitably substituted aryl halide and a suitably substituted arylboronic acid (the Suzuki coupling reaction) or aryl halide and aryl trialkyltin (the Stille coupling reaction) are reacted in the presence of a Pd catalyst.

Where —A—B— is —$CHR^X$—$CHR^X$—, the 2 carbon alkyl linker is readily prepared by reduction of the corresponding alkene linker (see above) by any number of common reagents including $H_2$(g) over Pd/C. Substituted analogs of the 2 carbon alkyl linker may be prepared by a variety of means known to a person of ordinary skill in the art. For example, the ketone linkage (see below) may be alkylated at the site neighboring the ketone functional group by combination with an electrophile in the presence of base. The ketone functional group may be converted to an amino group by reductive amination. The ketone linkage may also be converted to a substituted alkene linkage by reaction with the sodium salt of an appropriately substituted triphenylphosphonium halide reagent or similar. The hydroxyl group of the linkage sited as the precursor to the ketone may alternatively be converted to an ether or ester moiety by methods very familiar to a person of ordinary skill in the art.

Where —A—B— is —$CHR^Y$—O— or —O—$CHR^Y$—, the ether linker may be prepared by any of three methods. In the first method, a suitably substituted aryl alcohol may be combined in the presence of base with an appropriately substituted halomethyl arene. In the second method, an appropriately substituted aryl alcohol may be combined with an appropriately substituted hydroxymethyl arene in the presence of triphenylphosphine and diethyl azodicarboxylate (the Mitsunobu reaction). In the third method, an appropriately substituted aryl halide may be combined with an appropriately substituted hydroxymethyl arene in the presence of sodium tert-butoxide and a Pd-based catalyst (Buchwald coupling conditions).

Where —A—B— is —$NR^1$—C(=O)— or —C(=O)—$NR^1$—, the amide linker may be prepared by either of two methods. In the first method, a suitably substituted arylamine is combined with a suitably substituted arylcarboxylic acid in the presence of one of a variety of condensation reagents known to a person of ordinary skill in the art. In the second method, a suitably substituted arylamine is combined with a suitably substituted activated arylcarboxylic acid derivative, such as an arylcarboxylic acid halide.

Where —A—B— is —S(O)$_{0-2}$—CHR$^X$— or —CHR$^X$—S(O)$_{0-2}$—, the thioether linkage may prepared by the combination of a suitably substituted arenethiol with a suitably substituted halomethyl arene. The sulfoxide linkage is prepared by single oxidation of the thioether linkage by any of a variety of oxidation reagents known to a person of ordinary skill in the art. The sulfone linkage is prepared from either the thioether or the sulfoxide by treatment with any of a variety of oxidation reagents also known to a person of ordinary skill in the art.

Where —A—B— is —SO$_2$—NR$^1$— or —NR$^1$—SO$_2$—, the sulfonamide linkage may be prepared by reaction of a suitably substituted arylamine with a suitably substituted arenesulfonyl halide, which may in turn be first prepared from the appropriately substituted arenesulfonic acid by one of a variety of methods known to a person of ordinary skill in the art.

Where —A—B— is —C(O=)—CHR$^X$— or —CHR$^X$—C(=O)—, the ketone linkage is prepared by oxidation of the corresponding hydroxyl substituted linkage by the use of MnO$_2$ or any other of a variety of oxidizing reagents known to a person of ordinary skill in the art. The hydroxy substituted linkage can be prepared by reaction of a suitably substituted aryl aldehyde with a suitably substituted arylmagnesium halide, prepared in advance from the corresponding aryl halide (the Grignard reaction).

Where —A—B— is 1,2-cycloalkylene, the cycloalkylene linkage containing a double bond between the bonding ring carbons may be prepared by the reaction of a 1,2 dihalocycloalkene sequentially with the appropriately substituted arylboronic acids (Suzuki coupling reaction) or aryl trialkyltin reagents (Stille coupling reaction) in the presence of a Pd catalyst. The reduced cycloalkylene linkage may be prepared by reduction of the corresponding double-bonded linkage by reaction with H$_2$ (g) over Pd/C. In large part the cycloalkylene linkages where there are hetero atom(s) in the ring may be prepared in the same manner. Additional methods commonly used by persons of ordinary skill in the art to prepare a variety of 1,2-diaryl substituted cyclic moieties, too numerous to describe in detail here, can be found in "Heterocyclic Chemistry, 2$^{nd,}$ ed." T. L. Gilchrist, 1992, Longman Scientific and Technical, Essex; and "Heterocyclic Chemistry, 3d ed." J. A. Joule, K. Mills, and G. F. Smith, 1995, Chapman and Hall, London.

Under some circumstances, it may be appropriate to form the biphenyl linkage after forming the —A—B— linkage, as is shown in Example 1.

When the compound contains a biphenyl ether, as in formula II, it may be prepared by any of four methods. In the first method, a suitably substituted hydroxy arene is combined with a suitably substituted aryl fluoride or nitroarene in the presence of base. In the second method, a suitably substituted hydroxy arene is reacted with an appropriately substituted arylboronic acid under Evans conditions, i.e. in the presence of an appropriate copper-based catalyst. In the third method, a suitably substituted hydroxy arene is reacted with a suitably substituted aryl halide under Buchwald coupling conditions, i.e. in the presence of an appropriate palladium-based catalyst. In the fourth method an aryl vinyl ether is reacted with an appropriately substituted pyrone to form a cycloadduct (the Diels-Alder reaction), which subsequently undergoes the elimination of carbon dioxide to afford the biphenyl ether.

When the linker is of the form —X—A—B—, similar techniques may be used. A representative few are as follows:

When —X—A—B— is —CHR$^X$—CH(OH)—CHR$^Y$—, the 2-hydroxypropyl linkage may be prepared by the reaction of a suitably substituted arylacetaldehyde with a suitably substituted arylmethylmagnesium halide, prepared from the corresponding arenylmethyl halide (the Grignard coupling reaction).

When —X—A—B— is —CHR$^X$—NR$^1$C(=O)—, the amidomethyl linkage may be prepared by the reaction of a suitably substituted arenecarboxylic acid or activated arenecarboxylic acid derivative with an appropriately substituted aminomethylarene, under conditions described above for the A-B linked amide case. When —X—A—B— is —CHR—C(=O)—NR$^1$—, the amidomethyl linkage may be prepared by the reaction of a suitably substituted areneacetic acid or activated areneacetic acid derivative with an appropriately substituted aminoarene, under the same conditions. When —X—A—B— is —CH$_2$—CHR$^X$—NR$^1$—C(=O)—, the amidoethyl linkage may be prepared by the reaction of a suitably substituted arenecarboxylic acid or activated arenecarboxylic acid derivative with an appropriately substituted aminoethylarene, and when —X—A—B— is —CH$_2$—CHR$^X$—C(=O)—NR$^1$—, the amidoethyl linkage may be prepared by the reaction of a suitably substituted arenepropionic acid or activated arenepropionic acid derivative with an appropriately substituted aminoarene, under the same conditions.

When —X—A—B— is —CHR$^Y$—O—CHR$^Y$—, the C—O—C ether linkage may prepared by combination of the appropriately substituted hydroxymethyl arene with the appropriately substituted halomethyl-, methanesulfonyloxy-, or p-toluenesulfonyloxymethyl arene in the presence of base; and similarly when —X—A—B— is —CH$_2$—CHR$^Y$—O—CHR$^Y$—.

It will be evident that the biphenyl linkage may be formed either before or after the formation of the —X—A—B— linkage: Example 2 describes a synthesis in which the biphenyl linkage is formed after the formation of the —X—A—B— linkage.

It will also be evident that the phenyl rings may be substituted with substituents inert to the reaction conditions (or substituents protected against the reaction conditions associated with formation of the compound skeleton, where the protecting group can be removed without adverse effect on the remainder of the compound) without affecting the reactions described.

When a substituent is, for example, a carboxylic acid, it will typically be protected throughout the synthesis as an alkyl, e.g. C$_{1-4}$ alkyl ester, typically the methyl ester; with the ester being removed in the final deprotection step by reaction with an aqueous base, such as aqueous lithium hydroxide. When a substituent is or contains an amine or guanidino group, it will typically be protected with a typical amine-protecting group well known to a person of ordinary skill in the art, such as tert-butoxycarbonyl (BOC), benzyloxycarbonyl (CBZ), 9-fluorenylmethoxycarbonyl (FMOC), and the like, if needed, with the protecting group being removed in the final deprotection step by such methods as are conventional for removal of these amine-protecting groups. Under some circumstances, a carboxylic acid may be protected as an ester that is differentially removable, i.e. removable under circumstances where other carboxyl groups remain protected. When a substituent is a hydroxy group, it will typically be protected with a typical hydroxy-protecting group such as a tertiary silyl group, e.g. tert-butyldimethylsilyl. The choice of suitable protecting groups for substituents during the syntheses will be within the skill of a person of ordinary skill in the art having regard to that skill and this disclosure.

It will be apparent to a person of ordinary skill in the art, having regard to that skill, this disclosure, and the references cited herein, that generally any one of several different methods may be employed for the synthesis of a selected compound of this invention. For convenience, the synthesis may well be chosen based on the availability or cost of the starting materials and reagents for the methods available for that compound, or considering the number of steps necessary for the method. For example, if an appropriately substituted biphenyl or biphenyl ether is readily available or synthesizable, it may well be convenient to form the biphenyl/biphenyl ether linkage before formation of the —A—B— or —X—A—B— linkage; but otherwise it may be preferable to form the biphenyl or biphenyl ether linkages later. A person of ordinary skill in the art, having regard to that skill, this disclosure, and the references cited herein, will be able to prepare desired compounds of formula I without undue experimentation.

EXAMPLES

The following non-limiting examples illustrate the invention. All commercially available materials were used as received. All synthesized compounds were characterized by $^1$H NMR (Bruker DMX 400 MHz Spectrometer) and high-performance liquid-chromatography/mass-spectroscopy (HPLC-MS, Hewlett-Packard Series 1100 MSD), and judged to be at least 95% pure before testing in enzymatic assays.

Example 1

4-Fluoro-4'-[(4-hydroxy-3-methoxy)phenethyl]biphenyl (7)

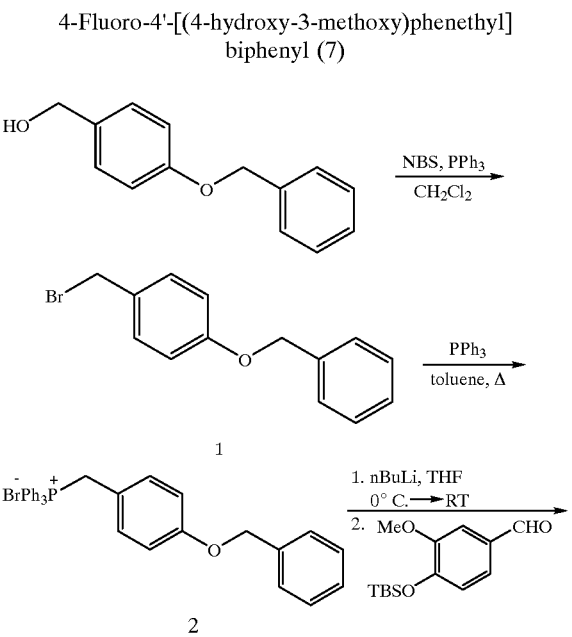

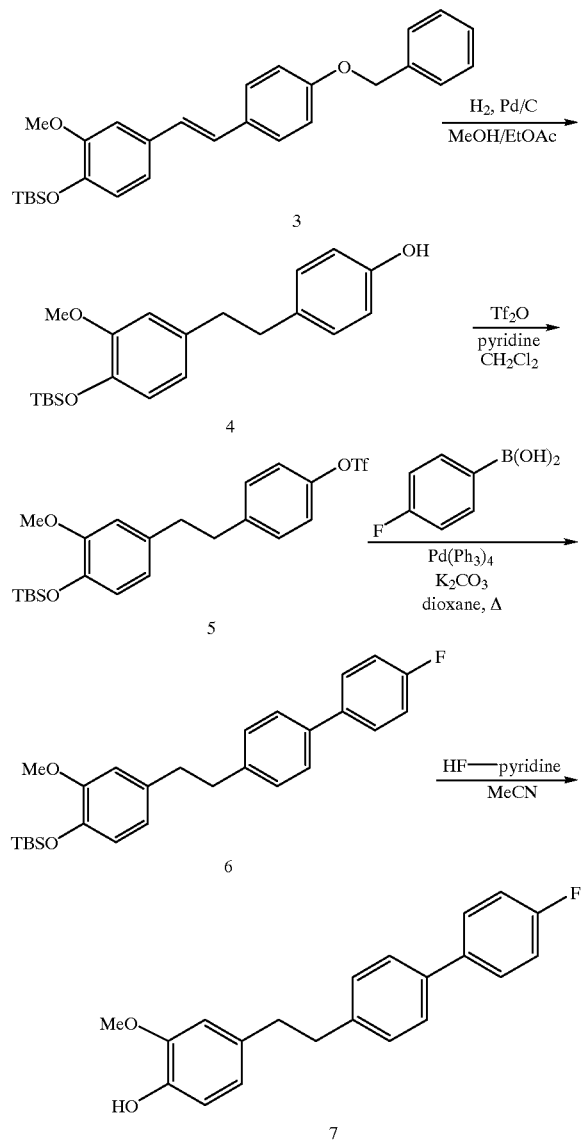

4-Benzyloxybenzyl bromide (1)

To 4-benzyloxybenzyl alcohol (8.1 g, 37.8 mmol) in dichloromethane (160 mL) was added N-bromosuccinimide (7.4 g, 41.6 mmol) followed by portionwise addition of triphenylphosphine (10.9 g, 41.6 mmol). The reaction mixture was stirred at room temperature for 5 minutes, and was then concentrated in vacuo. Purification by flash chromatography, eluting with 80:20 hexanes/ethyl acetate, provided 9.7 g (92%) of 1 as a white solid.

4-Benzyloxybenzyl triphenylphosphonium bromide (2)

To bromide 1 (9.7 g, 35.0 mmol) in toluene (300 mL) was added triphenylphosphine (10.1 g, 38.5 mmol). The reaction was stirred at reflux overnight. The reaction mixture was cooled to room temperature and the precipitate was filtered, washed twice with diethyl ether, and dried in vacuo to afford 17.4 g (92%) of 2 as a white solid.

3-Methoxy-4-tert-butyldimethylsilyloxy-4'-benzyloxystilbene (3)

To triphenylphosphonium bromide 2 (20.1 g, 37 mmol) in anhydrous tetrahydrofuran (300 mL) at 0° C. under N$_2$ atmosphere was added dropwise n-BuLi (1.2 M in hexanes, 28.6 mL, 34.3 mmol) by syringe. The reaction mixture was warmed to room temperature and allowed to stir for 30 minutes, then again cooled to 0° C. tert-Butyldimethyl-silyl-protected vanillin (7.6 g, 28.6 mmol) in anhydrous tetrahydrofuran (50 mL) was slowly added. The heterogeneous mixture was warmed to room temperature and stirred overnight. The reaction was quenched with 1 M HCl and partitioned with ethyl acetate. The organic layer was separated, and the aqueous layer was extracted with ethyl acetate (3×). Organic portions were combined, dried over $Na_2SO_4$ and concentrated in vacuo to give 32 g brown solid. Purification by flash chromatography, eluting with 80:20-hexanes/ethyl acetate, afforded 12.7 g (99%) 3 as a clear oil which was a mixture of cis- and trans- isomers.

4-(3-Methoxy-4-(tert-butyldimethylsilyloxy)phenethyl)phenol (4)

To stilbene 3 (12.7 g, 28.6 mmol) in 50% methanol/ethyl acetate (110 mL) was added palladium (1 g, 10 wt. % on activated carbon). The reaction vessel was equipped with a balloon of hydrogen gas and stirred overnight at room temperature and atmospheric pressure. Additional palladium (0.5 g) was added and the reaction was stirred for an additional 4 hours under hydrogen. The reaction mixture was filtered over diatomaceous earth (Celite). The Celite was washed thoroughly with methanol, and the resulting filtrate was concentrated in vacuo to give 16 g gray oil. Purification by flash chromatography, eluting with 90:10-hexanes/ethyl acetate, provided 9.5 g (93%) clear oil.

4-(3-Methoxy-4-(tert-butyldimethylsilyloxy)phenethyl)phenyl trifluoromethyl sulfonate (5)

To phenol 4 (2 g, 5.6 mmol) in dichloromethane (25 mL) was added pyridine (1.2 mL, 14.5 mmol). The solution was cooled to 0° C. and triflic anhydride (1.2 ml, 7.3 mmol) in dichloromethane (2 mL) was added dropwise. The reaction was warmed to room temperature and stirred 1 hour. The reaction was diluted with dichloromethane, partitioned with water, and the organic layer was separated. The aqueous portion was extracted with dichloromethane (2×), and the combined organic layer was washed with 1 M HCl (1×), saturated $NaHCO_3$ (1×), dried over $Na_2SO_4$ and concentrated in vacuo to afford 2.6 g 5 (96%) as a clear oil.

4-Fluoro-4'-[(3-methoxy-4-(tert-butyldimethylsilyloxy)phenethyl)]biphenyl (6)

To triflate 5 (350 mg, 0.71 mmol) in dioxane (3 mL) was added 4-fluorophenylboronic acid (110 mg, 0.79 mmol), $K_2CO_3$ (2 M, 713 μL, 1.43 mmol), and $Pd(PPh_3)_4$ (30 mg, 0.03 mmol). The reaction mixture was stirred at reflux for 2 hours. The reaction was cooled to room temperature, diluted with ethyl acetate and partitioned with water. The organic layer was separated and the aqueous layer was extracted with ethyl acetate (3×). The combined organic layer was washed with 1 M NaOH (1×), dried over $Na_2SO_4$ and concentrated in vacuo to give 441 mg brown residue. Purification by flash chromatography, eluting with 90:10-hexanes/ethyl acetate, provided 263 mg 6 (85%) as a white solid.

4-Fluoro-4'-[(4-hydroxy-3-methoxy)phenethyl]biphenyl (7)

To biphenyl 6 (117 mg, 0.27 mmol) in acetonitrile (1 mL) was added HF-pyridine (25 wt. % in acetonitrile, 2 mL). The reaction was stirred at room temperature overnight. The reaction was diluted with dichloromethane and partitioned with water. The organic layer was separated and the aqueous layer was extracted with dichloromethane (2×). The combined organic layer was washed with saturated $NaHCO_3$ (1×), 1 M HCl (1×), dried over $Na_2SO_4$ and concentrated in vacuo to give 143 mg white solid. Purification by flash chromatography, eluting with 80:20 hexanes/ethyl acetate, provided 52 mg (60%) 7 as a white solid. $^1$H NMR (400 MHz, $CD_3OD$): δ7.56–7.58 (m, 2H), 7.49–7.55 (m, 2H), 7.27 (d, 2H, J=7.8 Hz), 7.13–7.17 (m, 2H), 6.89 (d, 1H, J=8.0 Hz), 6.74 (d, 1H, J=8.0 Hz), 6.67 (d, 1H, J=1.3 Hz), 5.54 (s, 1H), 3.87 (s, 3H), 2.92–2.97 (m, 4H). HPLC-MS: 323 (M+1).

Similar methods were used to prepare:

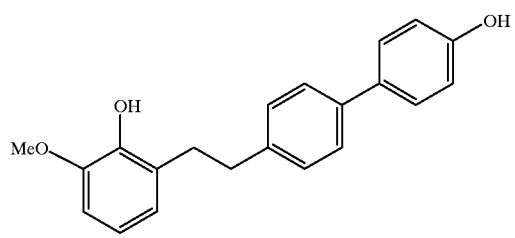

4-Hydroxy-4'-[(2-hydroxy-3-methoxy)phenethyl]biphenyl $^1$H NMR (400 MHz, $CD_3OD$): δ7.44 (m, 4H), 7.21 (d, 2H, J=8.0 Hz), 6.83 (d, 2H, J=8.0 Hz), 6.77–6.61 (m, 3H), 3.85 (s, 3H), 2.88 (m, 4H). HPLC-MS: 321 (M+1).

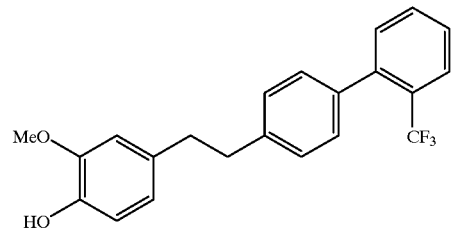

2-Trifluoromethyl-4'-[(4-hydroxy-3-methoxy)phenethyl]biphenyl $^1$H NMR (400 MHz, $CDCl_3$): δ7.79 (d, 1H, J=7.7 Hz), 7.59–7.65 (m, 1H), 7.45–7.55 (m, 1H), 7.36 (d, 1H, J=7.5 Hz), 7.23–7.30 (m, 4H), 6.91 (d, 1H, J=8.0 Hz), 6.75 (d, 1H, J=8.0 Hz), 6.66 (d, 1H, J=1.3 Hz), 5.57 (s, 1H), 3.87 (s, 3H), 2.97–2.99 (m, 4H). HPLC-MS: 373 (M+1).

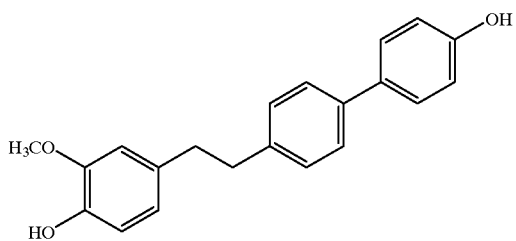

4-Hydroxy-4'-[(4-hydroxy-3-methoxy)phenethyl]biphenyl $^1$H NMR (400 MHz, $CD_3OD$): δ7.41(m, 4H), 7.16(d, 2H, J=8.0 Hz), 6.82(d, 2H, J=8.5 Hz), 6.68(d, 1H, J=8.0 Hz), 6.65(s, 1H), 6.61(d, 1H, J=8.0 Hz), 3.75(s, 3H), 2.88–2.86 (m, 4H). HPLC-MS: 321 (M+1).

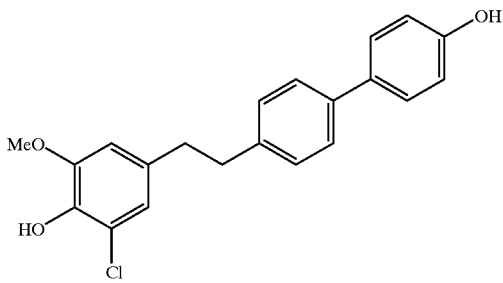

4-Hydroxy-4'-[(3-chloro4-hydroxy-5-methoxy) phenethyl]biphenyl

¹H NMR (400 MHz, CD₃OD): δ7.42 (m, 4H), 7.16 (d, 2H, J=8.0 Hz), 6.83 (d, 2H, J=8.0 Hz), 6.72 (s, 1H), 6.52 (s, 1H), 3.75 (s, 3H), 2.86–2.66 (m, 4H). HPLC-MS: 356 (M+1).

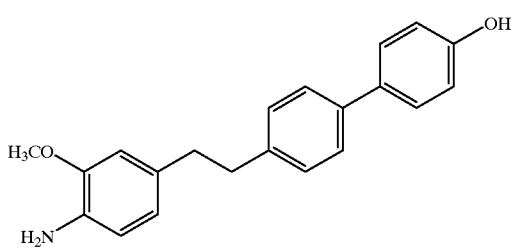

4-Hydroxy-4'-[(4-amino-3-methoxy)phenethyl] biphenyl

¹H NMR (400 MHz, CD₃OD): δ7.41(d, 4H, J=7.0 Hz), 7.16(d, 2H, J=7.9 Hz), 6.83(d, 2H, J=8.5 Hz), 6.67(d, 1H, J=7.6 Hz), 6.59(s, 1H), 6.58(d, J=8.0 Hz), 3.75(s, 3H), 2.87–2.81(m, 4H). HPLC-MS: 320 (M+1).

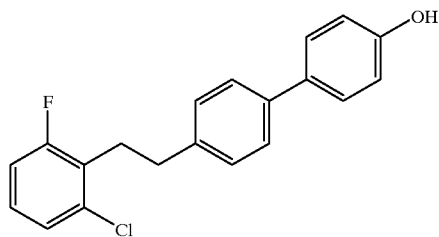

4-Hydroxy-4'-[(2-chloro-6-fluoro)phenethyl] biphenyl

¹H NMR (400 MHz, d-acetone): δ7.45–7.41 (m, 4H), 7.21–7.18 (m, 4H), 7.04 (m, 1H), 6.83 (d, 2H, J=8.5 Hz), 3.07 (t, 2H, J=8.1 Hz), 2.85 (t, 2H, J=8.1 Hz). LC-MS: 327 (M+1).

Other compounds may be similarly prepared.

By reacting the phenol (4) from the reaction scheme given earlier with phenylboronic acid or p-tolylboronic acid under Evans conditions (i.e. in the presence of a copper-based catalyst), and deprotecting, there were prepared:

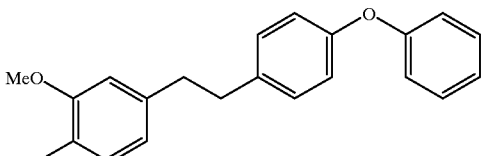

4-[(4-hydroxy-3-methoxy)phenethyl]phenyl phenyl ether

¹H NMR (400 MHz, CDCl₃): δ7.37–7.41 (m, 2H), 7.13–7.21 (m, 3H), 7.01–7.08 (m, 4H), 6.93 (d, 1H, J=8.0 Hz), 6.76 (d, 1H, J=8.1 Hz), 6.70 (s, 1H), 5.65 (s, 1H), 3.89 (s, 3H), 2.93 (s, 4H). HPLC-MS: 321 (M+1).

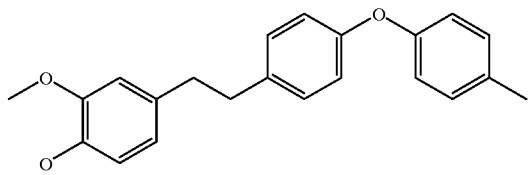

4-[(4-hydroxy-3-methoxy)phenethyl]phenyl 4-tolyl ether

¹H NMR (400 MHz, CDCl₃): δ7.10–7.14 (m, 4H), 6.89–6.92 (m, 4H), 6.84 (d, 1H, J=8.0 Hz), 6.69 (d, 1H, J=8.0 Hz), 6.62 (d, 1H, J=1.6 Hz), 3.80 (s, 3H), 2.85 (m, 4H), 2.31 (s, 3H). HPLC-MS: 335 (M+1).

Other biphenyl ether compounds may be similarly prepared.

Example 2

4-Fluoro-4'-[(4-hydroxy-3-methoxy) benzylaminocarbonyl]biphenyl (2)

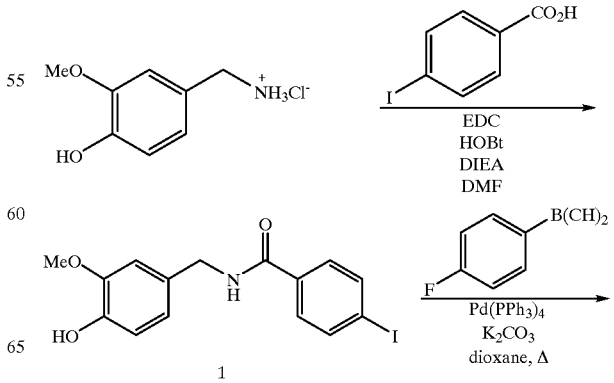

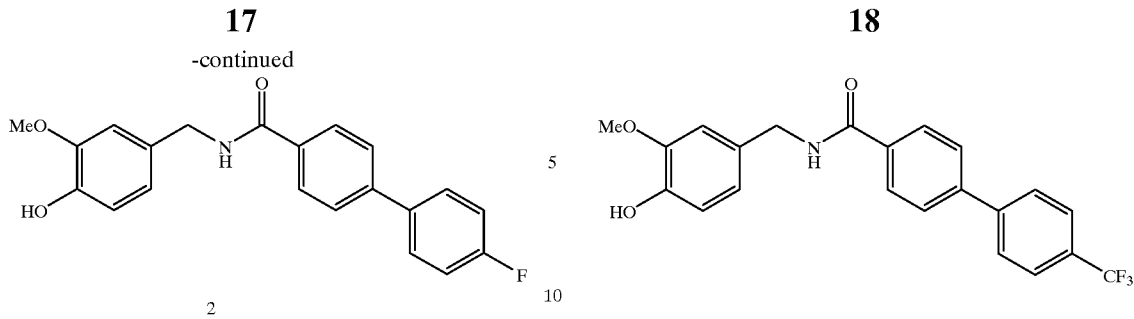

2

To 4-iodobenzoic acid (3.27 g, 13.2 mmol) in N,N'-dimethylformamide (50 mL) was added 1-(3-dimethylaminopropyl)-3-ethylcarbodiimide hydrochloride (2.78 g, 14.5 mmol), hydroxybenzotriazole monohydrate (2.22 g, 14.5 mmol) and di(isopropyl)ethylamine (5.05 mL, 29 mmol). To the activated acid solution was added 4-hydroxy-3-methoxybenzylamine hydrochloride (2.5 g, 13.2 mmol), and the reaction was stirred at room temperature for 1 hr. After 1 hour, solvent was removed in vacuo. The resulting residue was partitioned between ethyl acetate and 1 M HCl. A large amount of insoluble white material was collected by filtration and washed with diethyl ether (2×) and dried to afford 3.55 g (70%) of amide intermediate 1, which was used without further purification.

To amide 1 (268 mg, 0.70 mmol) and 4-fluorophenylboronic acid (108 mg, 0.77 mmol) in dioxane (3 mL) was added $K_2CO_3$ (700 µL, 1.40 mmol, 2M in $H_2O$) followed by $Pd(PPh_3)_4$ (30 mg, 0.03 mmol). The reaction was stirred at reflux for 1 hour. The mixture was cooled to room temperature, diluted with ethyl acetate and partitioned with water. The organic layer was separated, and the aqueous portion was extracted with ethyl acetate (3×). The combined organic layer was washed with 1 M HCl (1×), saturated $NaHCO_3$ (1×), dried over $Na_2SO_4$, and concentrated in vacuo to give 483 mg crude brown solid. Purification via reverse phase preparative HPLC afforded the final compound 2. $^1$H NMR (400 MHz, $CD_3OD$): δ7.93 (d, 1H, J=8.4 Hz), 7.68–7.71 (m, 4H), 7.19–7.23 (m, 2H), 6.98 (m, 1H), 6.79–6.83 (m, 2H), 4.52 (s, 2H), 3.86 (s, 3H). HPLC-MS: 352 (M+1).

Similar methods were used to prepare:

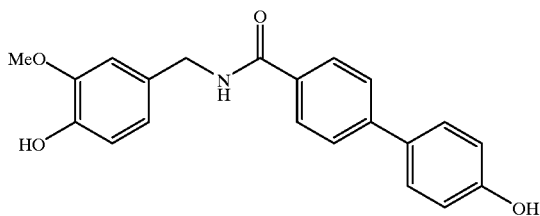

4-Hydroxy-4'-[(4-hydroxy-3-methoxy)benzylaminocarbonyl]biphenyl $^1$H NMR (400 MHz, $CDCl_3$): δ7.85 (d, 2H, J=7.7 Hz), 7.62 (d, 2H, J=7.6 Hz), 7.52 (d, 2H, J=7.7 Hz), 6.89–6.96 (m, 5H), 4.61 (d, 2H, J=5.3 Hz), 3.91 (s, 3H), 2.67 (s, 1H). HPLC-MS: 350 (M+1).

4-Trifluoromethyl-4'-[(4-hydroxy-3-methoxy)benzylaminocarbonyl]biphenyl $^1$H NMR (400 MHz, $CD_3OD$): δ7.98 (d, 2H, J=8.4 Hz), 7.88 (d, 2H, J=8.2 Hz), 7.77–7.81 (m, 3H), 6.99 (s, 1H), 6.84–6.86 (m, 1H), 6.78–6.80 (m, 1H), 4.50 (s, 2H), 3.86 (s, 3H). HPLC-MS: 402 (M+1).

Other compounds were similarly prepared.

Example 3

Inhibition of IL-4/IL-4R binding (STAT6 phosphorylation protocol)

Cell Culture. Ramos cells were grown in RPMI medium supplemented with 10% fetal bovine serum and antibiotics. Cells were split to 0.5 to 0.8×10$^6$ cells/mL on the day before the assay. On the day of the assay, the cell concentration is approximately 1×10$^6$ cells/mL.

The concentration of IL-4 used in the assay was determined by carrying out a dose-response curve according to the protocol detailed below. IL-4 concentrations between 0.25 and 0.5 ng/mL result in STAT6 activation that is in the linear range of the assay.

Compound Testing. Compound testing was carried out in the absence of serum. The samples, made up as in the table (1 mL), were preincubated in 15 mL polypropylene conical tubes (Corning) at 37° C. for 30 minutes.

| Sample | Compound | Growth Media |
| --- | --- | --- |
| No treatment | None | 1 mL RPMI no serum |
| IL-4 (0.25 ng/mL, final conc.) + vehicle | 2 µL DMSO | 1 mL RPMI no serum + 0.25 ng/mL IL-4 |
| IL-4 (0.25 ng/mL, final conc.) + test compound | 2 µL of test compound in DMSO (stock conc.: 2, 0.4, 0.08, 0.016 mM) | 1 mL RPMI no serum + 0.25 ng/mL IL-4 |

The Ramos cell concentration was determined; and the cells were centrifuged at 800×g at room temperature for 5 minutes. The cells were resuspended in pre-warmed RPMI medium (without serum) to a concentration of 10×10$^6$ cells/mL. To each sample (1 mL) was added 1 mL of the cell suspension;

and the samples were incubated at 37° C. for 30 minutes. Protein Extracts. The samples were centrifuged at 800×g at room temperature for 5 minutes. All medium was carefully removed from the cell pellet, which was placed on ice. The cells were then lysed with 50 µl of RIPA buffer containing protease and phosphatase inhibitors [150 mM NaCl, 50 mM Tris pH 8.0, 1.0% NP-40, 0.5% deoxycholate, 0.1% sodium dodecyl sulfate, 10 µg/mL aprotinin, 10 µg/mL antipain, 5 µg/mL leupeptin, 1 mg/mL Pefablock SC, 50 mM NaF, 80 mM sodium glycerophosphate, and 2 mM sodium vanadate (heat activated stock solution)].

The lysed cells were let'sit on ice for 5–15 minutes, the pipetted several times and transferred to microcentrifuge tubes. The cells were fully lysed by carrying out 2 freeze (dry ice) thaw (room temperature) cycles or sonicating the extract on ice for 10 seconds with a probe sonicator, then centrifuged in a Brinkmann mucrocentrifuge at full speed at 4° C. for 15 minutes. The supernatant was removed and transferred to another tube; the protein extract was passed through a 26 gauge needle to completely shear all DNA in the extracts, and the protein concentration was quantitated using Bio-Rad protein assay dye reagent (Bio-Rad Laboratories, catalog #500–0006).

Immunoblotting. Protein extract (20 μg) was loaded onto a Novex (Novex, San Diego) mini-protein gel (NuPAGE gel, 4–12%) according to the manufacturer's instructions; and the gel subjected to electrophoresis at 180 V for 1 hour in MOPS buffer (supplied by Novex). The gel was transferred to Novex PVDF membrane according to manufacturer's instructions. The PVDF membrane was blocked with 5% non-fat dry milk (NFDM) in TBST (8.00 g/L NaCl, 24.2 g/L Tris-base, 0.5% Tween 20, pH 7.6) for 1 hour.

Primary antibodies (Phospho STAT6, New England Biolabs) were diluted at 1:1000 in 5% BSA in TBST. The antibodies were incubated with the blot overnight at 4° C.; and the blot washed twice with TBST for 15–30 minutes each at room temperature.

The blot was then incubated with the appropriate secondary antibody (HRP conjugated goat anti-rabbit antibodies, Zymed, South San Francisco, Calif.) at 1:1000 in 0.5% NFDM in TBST for 2 hr at RT, and washed twice with TBST for 15–30 minutes each at room temperature. The blot was developed using ECL (Amersham International) plus Western blotting detection reagents in accordance with the manufacturer's instructions, and exposed to single emulsion Biomax film for 10 seconds to 10 minutes.

Compounds of this invention were active in this assay.

While this invention has been described in conjunction with specific embodiments and examples, it will be apparent to a person of ordinary skill in the art, having regard to this disclosure, that equivalents of the specifically disclosed materials and techniques will also be applicable to this invention; and such equivalents are intended to be included within the following claims.

What is claimed is:

1. A compound of formula I or formula II:

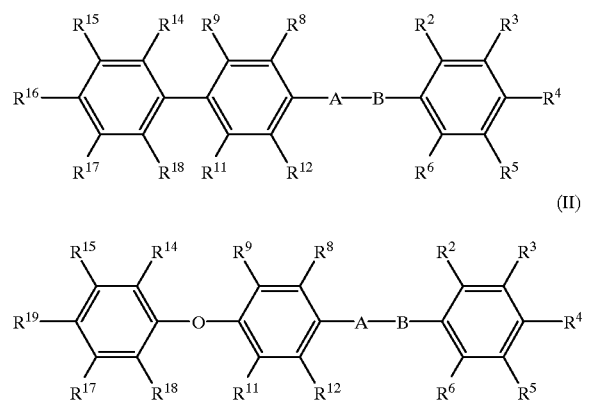

where:

A—B is selected from the group consisting of —CHR$^X$—CHR$^X$—, —CR$^Y$=CR$^Y$—, —CHR$^Y$—O—, —O—CHR$^Y$—, NR$^1$—C(=O)—, —C(=O)—NR$^1$, —S(O)$_{0-2}$—CHR$^X$—, —CHR$^X$—S(O)$_{0-2}$—, —SO$_2$—NR$^1$—, —NR$^1$—SO$_2$—, —C(=O)—CHR$^X$—, —CHR$^X$—C(=O)—, and cycloalkylene;

each R$^X$ is independently selected from the group consisting of hydrogen, hydroxy, alkyl, haloalkyl, aminoalkyl, guanidinoalkyl, alkoxy, amino, alkylamino, dialkylamino, cycloamino, alkylcarbonylamino, guanidino, carboxy, alkoxycarbonyl, and tetrazole;

each R$^Y$ is independently selected from the group consisting of hydrogen, alkyl, haloalkyl, carboxy, and alkoxycarbonyl;

each R$^1$ is independently selected from the group consisting of hydrogen and lower alkyl;

R$^2$ is selected from the group consisting of hydrogen, halo and hydroxy;

R$^3$ is selected from the group consisting of optionally fluorinated methoxy and optionally fluorinated ethoxy;

R$^4$ is selected from the group consisting of hydrogen, hydroxy, amino, alkylamino, dialkylamino, and cycloamino;

R$^5$ is selected from the group consisting of hydrogen, halo, alkyl, haloalkyl, alkoxy, amino, alkylcarbonylamino, alkylsulfonylamino, benzenesulfonylamino, toluenesulfonylamino, carboxy, aminocarbonyl, alkylaminocarbonyl, dialkylaminocarbonyl, cycloaminocarbonyl, and alkoxycarbonyl;

R$^6$ is selected from the group consisting of hydrogen, halo and hydroxy;

R$^8$, R$^9$, R$^{11}$, R$^{12}$, R$^{14}$, R$^{15}$, R$^{17}$ and R$^{18}$ are independently selected from the group consisting of hydrogen, halo, alkyl, haloalkyl, methoxy, and ethoxy;

R$^{16}$ is selected from the group consisting of hydrogen, hydroxy, halo, haloalkyl, alkoxy, aminocarbonyl, alkylaminocarbonyl, carboxy, alkoxycarbonyl, —SO$_2$NR$^1_2$, and —NR$^1$SO$_2$R$^1$;

R$^{19}$ is selected from the group consisting of hydrogen, hydroxy, halo, haloalkyl, alkoxy, aminocarbonyl, alkylaminocarbonyl, carboxy, alkoxycarbonyl, —SO$_2$NR$^1_2$, and —NR$^1$SO$_2$R$^1$; in which:

(1) at least one of R$^2$, R$^4$, and R$^6$ is not hydrogen; and
(2) at least one of R$^{14}$, R$^{15}$, R$^{16}$, R$^{17}$, and R$^{18}$ in formulae I, III, IV, and VI, or at least one of R$^{14}$, R$^{15}$, R$^{17}$, R$^{18}$, and R$^{19}$ in formula II, is not hydrogen;

or a pharmaceutically acceptable salt thereof.

2. The compound of claim 1 that is a compound of formula III

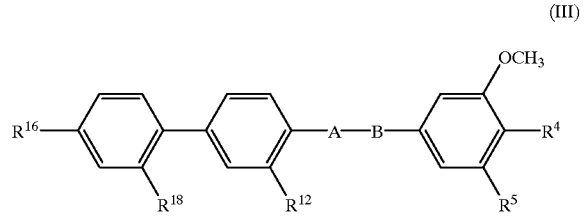

where:

A—B is —CHR$^X$—CHR$^X$—, —CHR$^Y$—O—, —O—CHR$^Y$—, —NR$^1$—C(=O)—, —C(=O)—NR$^1$, —SO$_2$—NR$^1$—, or —NR$^1$—SO$_2$—;

and R$^X$, R$^Y$, R$^4$, R$^5$, R$^{12}$, R$^{16}$, and R$^{18}$ are as in claim 1; or a pharmaceutically acceptable salt thereof.

3. The compound of claim 1 that is a compound of formula IV

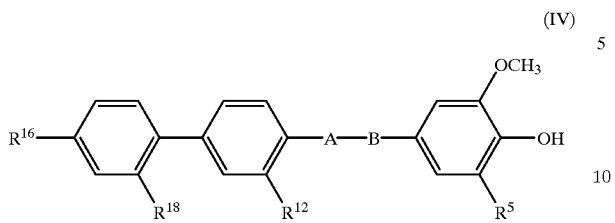

(IV)

where:
A—B is —CHR$^X$—CHR$^X$—, —CHR$^Y$—O—, or —O—CHR$^Y$—;
and R$^X$, R$^Y$, R$^5$, R$^{12}$, and R$^{18}$ are as in claim 1;
or a pharmaceutically acceptable salt thereof.

4. The compound of claim 1 that is a compound of formula V

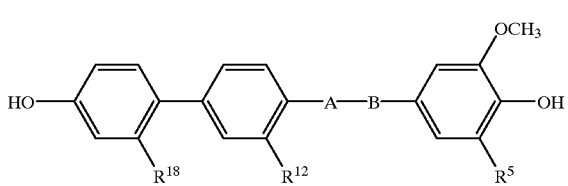

(V)

where:
A—B is —CHR$^X$—CHR$^X$—;
and R$^X$, R$^5$, R$^{12}$, R$^{16}$, and R$^{18}$ are as in claim 1;
or a pharmaceutically acceptable salt thereof.

5. A compound of formula VI

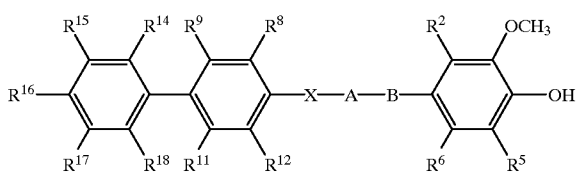

VI where:
X is selected from —CHR$^X$— and —CH$_2$—CHR$^X$—;
A—B is selected from the group consisting of —CHR$^X$—CHR$^X$—, —CR$^Y$=CR$^Y$—, —CHR$^Y$—O—, —O—CHR$^Y$—, —NR$^1$—C(=O)—, —C(=O)—NR$^1$, —S(O)$_{0-2}$—CHR$^X$—, —CHR$^X$—S(O)$_{0-2}$—, —SO$_2$—NR$^1$—, —NR$^1$—SO$_2$—, —C(=O)—CHR$^X$—, —CHR$^X$—C(=O)—, and cycloalkylene;
each R$^X$ is independently selected from the group consisting of hydrogen, hydroxy, alkyl, haloalkyl, aminoalkyl, guanidinoalkyl, alkoxy, amino, alkylamino, dialkylamino, cycloamino, alkylcarbonylamino, guanidino, carboxy, alkoxycarbonyl, and tetrazole;
each R$^Y$ is independently selected from the group consisting of hydrogen, alkyl, haloalkyl, carboxy, and alkoxycarbonyl;
each R$^1$ is independently selected from the group consisting of hydrogen and lower alkyl;

R$^2$ is selected from the group consisting of hydrogen, halo and hydroxy;
R$^5$ is selected from the group consisting of hydrogen, halo, alkyl, haloalkyl, alkoxy, amino, alkylcarbonylamino, alkylsulfonylamino, benzenesulfonylamino, toluenesulfonylamino, carboxy, aminocarbonyl, alkylaminocarbonyl, dialkylaminocarbonyl, cycloaminocarbonyl, and alkoxycarbonyl;
R$^6$ is selected from the group consisting of hydrogen, halo, and hydroxy;
R$^8$, R$^9$, R$^{11}$, R$^{12}$, R$^{14}$, R$^{15}$, R$^{17}$ and R$^{18}$ are independently selected from the group consisting of hydrogen, halo, alkyl, haloalkyl, methoxy, and ethoxy;
R$^{16}$ is selected from the group consisting of hydrogen, hydroxy, halo, haloalkyl, alkoxy, aminocarbonyl, alkylaminocarbonyl, carboxy, alkoxycarbonyl, —SO$_2$NR$^1_2$, and —NR$^1$SO$_2$R$^1$;
in which at least one of R$^{14}$, R$^{15}$, R$^{16}$, R$^{17}$, and R$^{18}$ is not hydrogen;
or a pharmaceutically acceptable salt thereof.

6. A pharmaceutical composition comprising:
(a) a therapeutically effective amount of a compound of claim 1; and
(b) a pharmaceutically acceptable excipient.

7. A pharmaceutical composition comprising:
(a) a therapeutically effective amount of a compound of claim 2; and
(b) a phamaceutically acceptable excipient.

8. A pharmaceutical composition comprising:
(a) a therapeutically effective amount of a compound of claim 3; and
(b) a pharmaceutically acceptable excipient.

9. A pharmaceutical composition comprising:
(a) a therapeutically effective amount of a compound of claim 4; and
(b) a pharmaceutically acceptable excipient.

10. A pharmaceutical composition comprising:
(a) a therapeutically effective amount of a compound of claim 5; and
(b) a pharmaceutically acceptable excipient.

11. A method of treating an animal having a disease capable of treatment by administration of an IL-4 antagonist, comprising administration to that animal of a therapeutically effective amount of a compound of claim 1.

12. A method of treating an animal having a disease capable of treatment by administration of an IL-4 antagonist, comprising administration to that animal of a therapeutically effective amount of a compound of claim 2.

13. A method of treating an animal having a disease capable of treatment by administration of a IL-4 antagonist, comprising administration to that animal of a therapeutically effective amount of a compound of claim 3.

14. A method of treating an animal having a disease capable of treatment by administration of a IL-4 antagonist, comprising administration to that animal of a therapeutically effective amount of a compound of claim 4.

15. A method of treating an animal having a disease capable of treatment by administration of a IL-4 antagonist, comprising administration to that animal of a therapeutically effective amount of a compound of claim 5.

* * * * *